United States Patent [19]

Charbonnier et al.

[11] 4,328,808
[45] May 11, 1982

[54] DEFIBRILLATOR WITH MEANS FOR DETERMINING PATIENT IMPEDANCE AND DELIVERED ENERGY

[75] Inventors: Francis M. Charbonnier; Paul V. Long, both of McMinnville, Oreg.

[73] Assignee: Hewlett-Packard Company, Palo Alto, Calif.

[21] Appl. No.: 195,558

[22] Filed: Oct. 9, 1980

[51] Int. Cl.³ .............................................. A61N 1/36
[52] U.S. Cl. .............................................. 128/419 D
[58] Field of Search .................................. 128/419 D

[56] References Cited
U.S. PATENT DOCUMENTS
3,860,009  1/1975  Bell et al. ........................ 128/419 D OTHER PUBLICATIONS
Stratbucker et al., "Rocky Mountain Engineering Society", 1965, pp. 57–61.

Primary Examiner—William E. Kamm
Attorney, Agent, or Firm—Stephen P. Fox

[57] ABSTRACT

A defibrillator apparatus applies defibrillation a shock pulse to a patient at a selected energy level. The peak current magnitude of the pulse is sensed and processed to produce an indication of the value of transthoracic load resistance presented by the patient during the pulse. Also produced is an indication of the energy actually delivered to the patient by the defibrillation pulse. An alarm is activated when patient transthoracic resistance exceeds a predetermined value, thereby to warn the operator to take corrective action before again attempting defibrillation.

14 Claims, 3 Drawing Figures

DEFIBRILLATOR WITH MEANS FOR DETERMINING PATIENT IMPEDANCE AND DELIVERED ENERGY

BACKGROUND OF THE INVENTION

The present invention relates generally to patient defibrillation apparatus and means for producing and displaying selected parameters during defibrillation.

A defibrillator is commonly used to administer a high voltage, direct current shock pulse through a pair of electrodes, or "paddles", which are placed in contact with the chest of a patient in cardiac distress. A selected, discrete quantity of energy is stored in a capacitor and then electrically discharged into the patient through the paddle circuit. The quantity of energy is typically selected on the basis of patient size, weight and condition.

One type of known defibrillator monitors and displays the magnitude of peak current in the discharge pulse during defibrillation. Measured peak current is one parameter used in assessing the performance of the defibrillator. Another useful parameter is the quantity of energy actually delivered to a patient during defibrillation. Known defibrillators display a parameter often termed "delivered energy"; however, the displayed quantity is in reality only the anticipated energy that would be applied to a patient in an assumed case. For example, it is assumed that the patient represents some selected nominal resistive load, say 50 ohms. Since the selected nominal load rarely matches actual load resistance, the energy value displayed is not an accurate representation of the energy actually delivered to a patient during defibrillation.

Actual external load resistance produced at the paddles during defibrillation is referred to as the patient's transthoracic resistance. Researchers have attempted to estimate this parameter from calculations of the integral of the output voltage waveform over time at the defibrillator paddles during discharge of the defibrillator storage capacitor. Such work has been reported by Ewy, et al., in a paper entitled "Canine Transthoracic Resistance", published in the Journal of Applied Physiology, Vol. 32, No. 1, January, 1972. The process of obtaining a voltage-time integral is difficult because it requires high speed, complex measuring and integration circuits.

Known defibrillators are incapable of monitoring and displaying the value of patient load resistance which occurs when the defibrillation shock pulse is administered. To the defibrillator operator, patient load resistance is a useful parameter for assessing the efficiency of defibrillation.

SUMMARY OF THE INVENTION

The present invention measures and displays the transthoracic resistance of a patient during a defibrillation pulse, and the energy actually delivered to the patient through the defibrillator paddles. On the basis of measured transthoracic resistance, there is indicated whether or not the defibrillator paddles have made satisfactory contact with the patient during defibrillation.

The illustrated embodiment of the invention senses the voltage across the defibrillator capacitor immediately prior to a defibrillation discharge pulse and correlates this voltage to the energy stored in the capacitor. Also sensed is the peak current applied to a patient through the defibrillator paddles during the defibrillation pulse. The peak current magnitude is normalized to the square root of the quantity of stored energy that is discharged during the pulse.

Normalized peak current is correlated to specific values of patient transthoracic resistance determined either empirically or mathematically. The value of transthoracic resistance is displayed on an annotating recorder for use by the defibrillator operator. Transthoracic resistance is also compared to a predetermined threshold value and when the resistance exceeds such value, an indicator warns of unsatisfactory contact between the patient and the defibrillator paddles.

The normalized peak current is also correlated to specific values representing transthoracic resistance as a proportion of the combined internal and external circuit resistance presented to the defibrillator storage capacitor during electrical discharge. The derived proportion is multiplied by the magnitude of energy stored in the capacitor to obtain the value of energy actually delivered to the patient during a defibrillation pulse. This energy value is displayed for use by the operator.

DESCRIPTION OF THE PREFERRED EMBODIMENT

Figure 1:
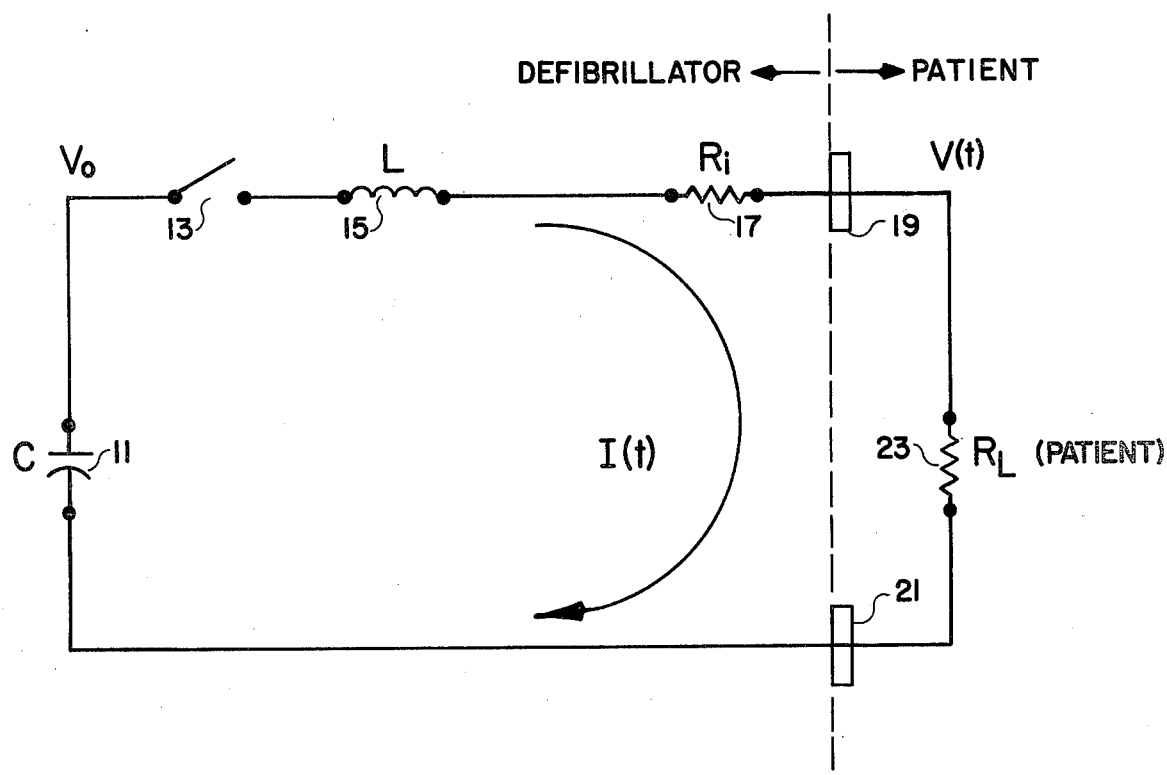
FIG. 1 is a schematic diagram of a basic defibrillator discharge circuit.

Referring now to FIG. 1 there is shown a schematic diagram of a typical heretofore known defibrillator discharge circuit. A capacitor 11 having a capacitance C stores a charge at a high voltage $V_0$, on the order of 5000 volts. When a switch 13 is closed, the charge is applied through the series connection of an inductor 15 having an inductance L and a resistance 17 internal to the defibrillator and having a resistance $R_i$. The discharge current path is completed through a first defibrillator paddle 19, the patient, and a second defibrillator paddle 21. The transthoracic resistance of the patient presented to the defibrillator paddles is represented by the resistance 23 having a value $R_L$. The defibrillation shock pulse applied to the patient when switch 13 is closed produces a current pulse I(t) which reaches a peak magnitude about one millisecond after the switch is closed.

The capacitance C and inductance L are chosen to provide the desired values of output voltage V(t) and current for a broad range of patients. This is achieved by assuming that the patient represents a nominal 50 ohm external load $R_L$, and then selecting circuit parameters to provide a critically damped discharge current into the patient of about 3–12 milliseconds duration. The energy discharged into the patient typically ranges from about 5–360 joules, depending on the size, weight and condition of the patient.

Figure 2:
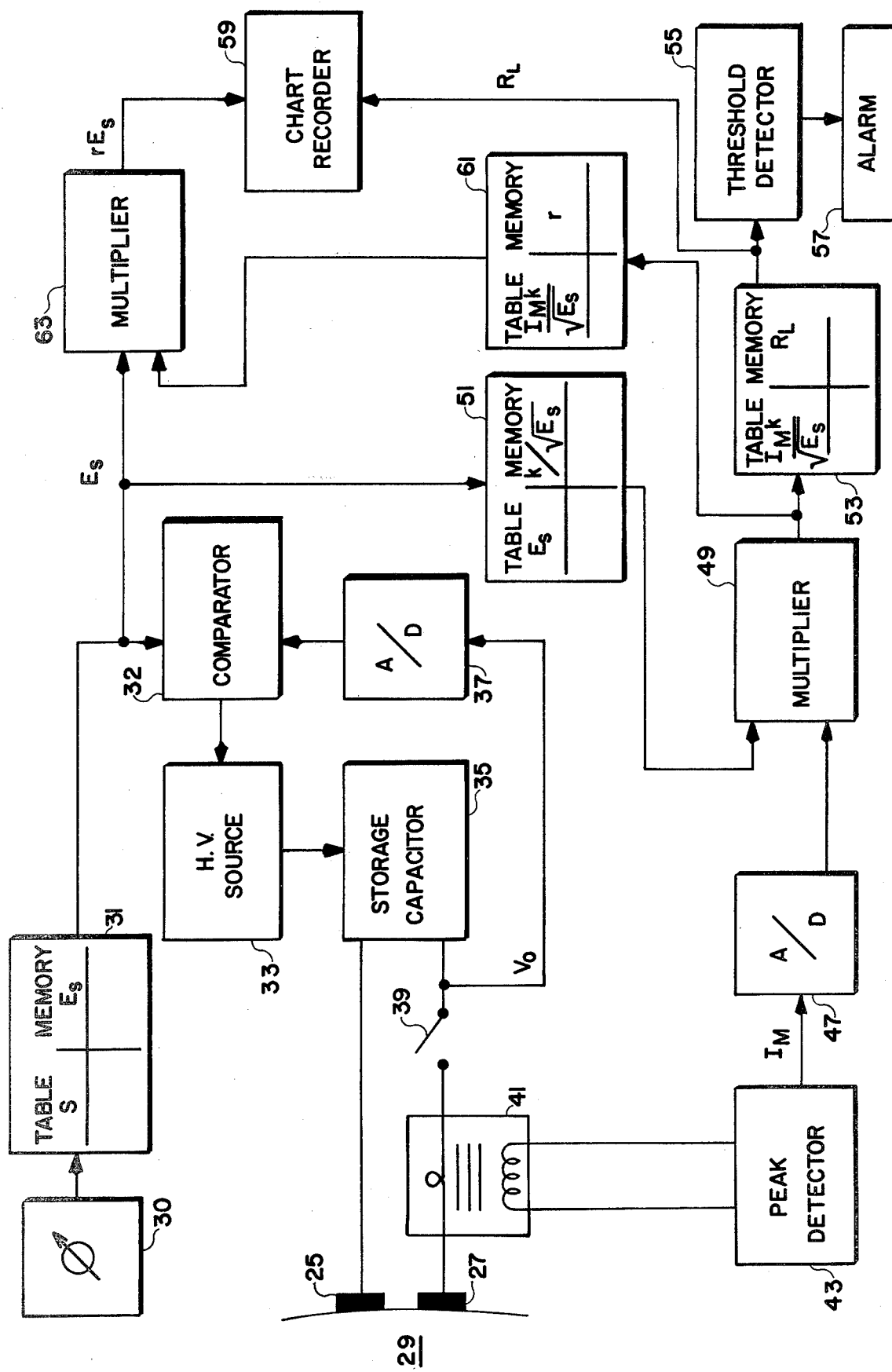
FIG. 2 is a block diagram of one embodiment of a defibrillator circuit constructed according to the principles of the invention.

FIG. 2 illustrates one embodiment of the invention. A pair of defibrillator paddles 25, 27 are applied to the chest of a patient 29 having a transthoracic resistance $R_L$. Prior to defibrillation of the patient, the value of his transthoracic resistance is not known to the defibrillator operator. On the basis of patient size, weight and condition, the defibrillator operator selects an appropriate discharge energy setting, say 200 joules, on a selector switch 30 having a digital output. The selector switch 30 provides a four-bit digital signal to the input of a read-only memory (ROM) 31 containing a look-up table that converts the setting S of switch 30 to an eight-bit digital signal representing the selected value of energy to be stored in the defibrillator capacitor, as hereinafter described. The output of ROM 31 is coupled to one input of a digital comparator 32 having an output which controls a high voltage source 33. The high voltage output from source 33 charges a defibrillator storage capacitor 35 to a voltage level $V_0$. This voltage is applied to the input of an analog to digital converter 37 and thence to the other input of digital comparator 32. In operation, the digital comparator 32 provides an output signal to the voltage source 33 which increases or decreases the capacitor charging voltage until the two inputs to comparator 32 are equal. At this point, the voltage $V_0$ on the storage capacitor 35 will have a value such that in the ideal case, the energy to be discharged by the capacitor into the patient during a defibrillation shock pulse equals the energy setting selected by the operator on the selector switch 30. The settings on selector switch 30 are calibrated on the assumption that the patient has a nominal 50 ohm transthoracic resistance. However, in reality, the actual value of patient resistance $R_L$ ranges from about 25 to 100 ohms. Consequently, the discharge energy selected by switch 30 is only an approximation of the energy actually delivered to the patient.

The circuit of the present invention enables the accurate determination and display to an operator of the actual patient transthoracic resistance $R_L$ and the actual energy $E_d$ delivered to the patient.

When it is desired to administer the defibrillation pulse, switch 39 is closed to discharge the storage capacitor 35 into the patient through the defibrillator paddles 25, 27. The discharge current to the patient typically reaches a peak magnitude $I_M$ within 2 milliseconds after the onset of the discharge pulse. Discharge current is sensed by a current transformer 41 having a primary winding in the main current path to the patient, and a secondary winding which provides a current signal to a peak detector 43. The peak current magnitude $I_M$ during discharge is sensed and held by peak detector 43. The analog current magnitude output from the peak detector 43 is applied to an analog to digital converter 47 and thence to a digital multiplier circuit 49, described hereinafter.

The digital output of analog to digital converters 37, 47 and the digital output of ROM 31 are in the form of eight-bit binary signals, each capable of representing 255 different values.

The digital output from ROM 31 represents the stored energy, $E_s$, in the capacitor 35. This stored energy signal in digital form is applied to the input of a read-only memory 51 containing a look-up table. ROM 51 is programmed so that each discrete value of stored energy $E_s$ corresponds to a value equal to the value of a scaling constant k divided by the square root of the value of stored energy $E_s$. In other words, for each specific digital value of $E_s$ applied to ROM 51, the look-up table in ROM 51 provides a digital output signal corresponding to a value $k/\sqrt{E_s}$. ROM 51 correlates values of stored energy to predetermined values of the reciprocal of the square root of stored energy in capacitor 35.

The output of ROM 51 is applied to one input of multiplier 49. The other input to the multiplier is the peak current signal $I_M$ received from the peak detector 43 described above. The two inputs are multiplied to provide a signal at the output of multiplier 49 which corresponds to the term $I_M k/\sqrt{E_s}$. This term represents the magnitude of the peak current applied to the patient, normalized to the square root of the defibrillation energy $E_s$ which has been set by the selector switch 30.

It has been found that the normalized peak current is a monotonic function of the total resistance in the defibrillation circuit path from the storage capacitor 35 through the defibrillation paddles to the patient 29. The total resistance is the sum of the known internal resistance of the defibrillator, $R_i$, and the unknown external transthoracic resistance of the patient $R_L$. For given values of inductance L, capacitance C and resistance $R_i$ in the defibrillation circuit path, each normalized value of peak current magnitude sensed during a defibrillation pulse has only one corresponding value of patient resistance $R_L$.

Figure 3:
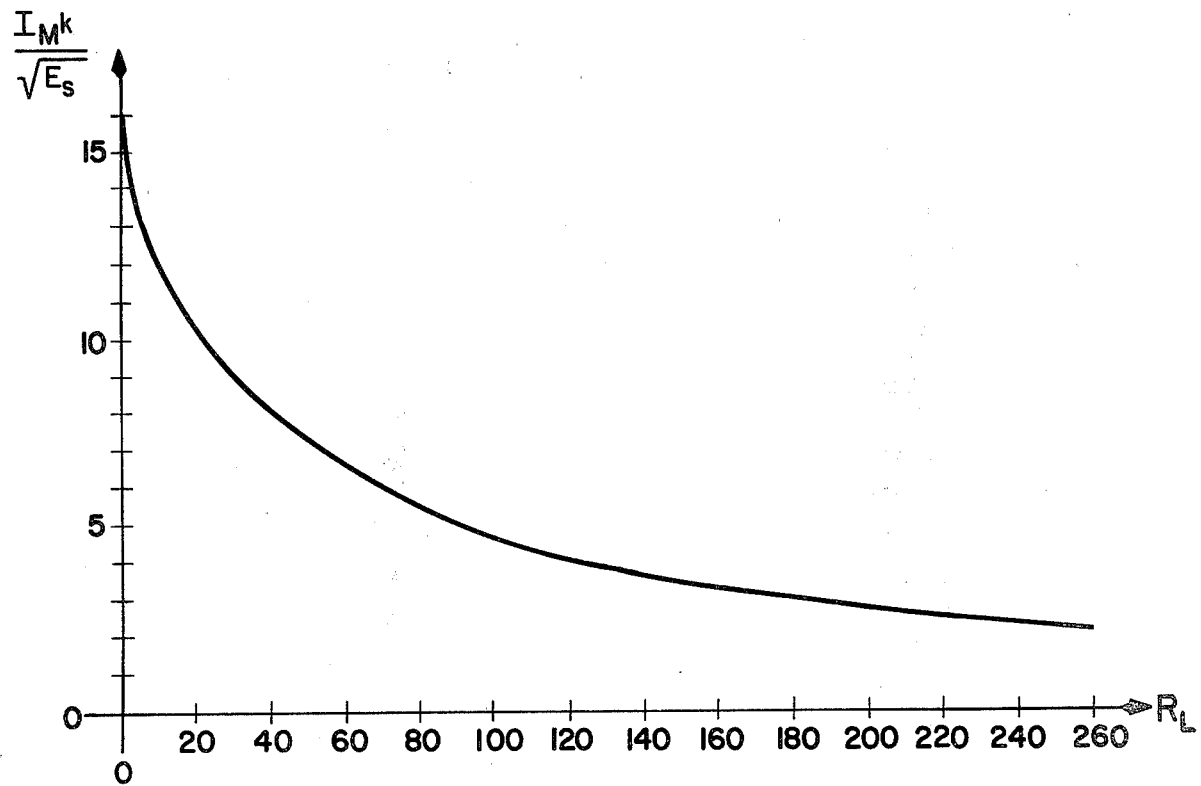
FIG. 3 is a graph illustrating the relationship between normalized peak current and patient load resistance.

The relationship between peak current magnitude and patient resistance $R_L$ is illustrated by the graph of FIG. 3. The curve may be obtained empirically by substituting specific known values of load resistance for the patient 29 and measuring the normalized peak current magnitude at the output of multiplier 49 for each value of known load resistance. Alternatively the curve of FIG. 3 may be obtained mathematically by using the following three equations for defibrillator discharge current, normalized to stored energy in capacitor 35, as a function of time in the RLC series circuit:

$$\frac{I(t)}{\sqrt{E_s}} = \frac{2\sqrt{2}}{R\sqrt{C}\sqrt{D}} e^{-\frac{R}{2L}t} \sinh \frac{R}{2L}\sqrt{D}\, t \quad \text{if} \quad \text{(Eq. 1)}$$

$$D > 0 \text{ (overdamped)}$$

$$\frac{I(t)}{\sqrt{E_s}} = \frac{2\sqrt{2}}{R\sqrt{C}\sqrt{-D}} e^{-\frac{R}{2L}t} \sin \frac{R}{2L}\sqrt{-D}\, t \quad \text{if} \quad \text{(Eq. 2)}$$

$$D < 0 \text{ (underdamped)}$$

$$\frac{I(t)}{\sqrt{E_s}} = \frac{\sqrt{2}}{L\sqrt{C}} t\, e^{-\frac{R}{2L}t} \quad \text{if } D = 0 \text{ (critically damped)} \quad \text{(Eq. 3)}$$

where $D = 1 - 4L/R^2C$, and where $R = R_i + R_L$, i.e., the sum of the internal defibrillator resistance $R_i$ and the external patient load resistance $R_L$. C is the capacitance of the storage capacitor 35 and L is the circuit inductance.

In each of the equations 1-3, the values of $R_i$, C, and L are known. The value of D is determined for a given value of $R_L$, say one ohm. Thereafter, the particular one of equations 1-3 corresponding to the value of D is solved in an iterative manner by inserting successive values of t changed by predetermined increments, e.g., 10 microseconds. The iterative solution will reveal the maximum value for normalized current which is the peak current magnitude $I_M/\sqrt{E_s}$. The process is repeated for additional selected values of $R_L$ until there are derived 255 values of normalized peak current magnitude $I_M/\sqrt{E_s}$ in terms of values of external resistance $R_L$. These value relationships are then inverted to obtain values of resistance $R_L$ in terms of normalized peak current magnitude $I_M/\sqrt{E_s}$.

A read-only memory 53 contains a look-up table which correlates each value of normalized peak current magnitude received from multiplier 49 to a specific value of patient transthoracic resistance $R_L$ derived either empirically or mathematically in the manner described hereinabove. Thus, for a given one of 255 specific values of normalized peak current sensed in the defibrillator discharge circuit, there is obtained at the output of ROM 53 a specific value of patient transthoracic resistance $R_L$. The value of resistance $R_L$ from ROM 53 is applied to a threshold detector circuit 55 which determines when the digital value of $R_L$ exceeds a predetermined threshold value. When the threshold value is exceeded, threshold detector 55 provides an output signal to activate an alarm 57, which may be an indicator light on the control panel of the defibrillator. Alternatively alarm 57 may provide an audible tone to the defibrillator operator.

The threshold limit of detector 55 is set to a value to detect abnormally high patient resistance values. Most patients have a transthoracic resistance in the range of 35 to 80 ohms. If the threshold detector limit is set at 100 ohms, for example, then the activation of alarm 57 will indicate that substantial additional resistance is present in the defibrillator circuit path during discharge due to a poor electrical contact between the defibrillator paddles 25, 27 and the patient 29. The alarm serves as an indication to the defibrillator operator that it is necessary to apply more conductive paste between the paddles 25, 27 and the patient, or to apply more pressure to the paddles, or to reposition the defibrillator paddles to insure better patient-paddle contact. Thereafter, another defibrillation attempt can be made, in order to achieve a more effective current discharge into the patient.

The output of ROM 53 is also coupled to the input of a strip chart recorder included as part of the defibrillator instrument. The specific value of transthoracic resistance $R_L$ is printed on the chart as an annotation. Thus, for each defibrillator discharge pulse, there is displayed for use by the operator a specific value of patient resistance.

The output of digital multiplier 49 is also applied to a read-only memory 61. The ROM 61 contains a look-up table which correlates output values of the normalized peak current magnitude $I_M k/\sqrt{E_s}$ to predetermined values which represent the ratio r of patient transthoracic resistance to total circuit resistance established in the current path through the defibrillator paddles to the patient. This ratio r is represented by the following equation:

$$r = R_L/(R_i + R_L) \qquad \text{(Eq. 4)}$$

Each of the possible 255 values of normalized peak current magnitude has a corresponding value for the ratio r. The different values for r are derived from Equation 4 using the known value of internal circuit resistance $R_i$ and the values of external patient resistance $R_L$ derived in the manner described above.

The output of ROM 61 is applied to one input of a digital multiplier 63. The other input of multiplier 63 is coupled to ROM 31 and receives the digital signal representing the energy $E_s$ stored in the defibrillator capacitor 35 prior to discharge into the patient. The output of multiplier 63 is a digital signal representing the proportion of the energy stored in capacitor 35 which is actually delivered to the patient. This delivered energy, $E_d$, is the portion of the energy stored in the capacitor 35 which is dissipated by the patient's transthoracic resistance. The remainder of the energy stored in capacitor 35 is dissipated by the internal circuit resistance $R_i$. The value of actual energy delivered to the patient is applied to chart recorder 59 and displayed for use by the operator.

In summary, it can be seen that the magnitude of the peak current applied to the patient during a defibrillation shock pulse is used to produce specific values of patient transthoracic resistance and energy actually delivered to the patient. Both patient resistance and delivered energy are displayed on a chart recorder immediately after administration of the shock pulse. A significant feature of the system is that the value of patient resistance detected for a given defibrillation shock pulse will trigger an audible or visual alarm to warn the defibrillator operator that the patient resistance detected was abnormally high and hence that there was poor contact between the defibrillator paddles and the patient. In the case where the poor paddle contact alarm is activated, the operator can then take corrective action and again attempt defibrillation to achieve more successful results.

We claim:

1. Patient defibrillator apparatus comprising:
   means for storing high voltage patient defibrillation energy;
   patient electrode means coupled to said energy storage means for applying a defibrillation shock pulse to a patient;
   first means coupled to said energy storage means for determining the magnitude of stored defibrillation energy to be applied to said patient electrode means;
   second means coupled to said electrode means for sensing and holding the magnitude of the peak current applied to a patient during a defibrillation shock pulse;
   third means coupled to said first means and said second means for determining the actual transthoracic resistance of a patient being defibrillated, in response to the magnitudes of stored defibrillation energy and peak current; and
   fourth means coupled to said first means and said third means for determining the proportion of said stored defibrillation energy actually delivered to a patient during defibrillation.

2. The apparatus of claim 1 further including:
   means responsive to said third means for detecting when transthoracic resistance of a patient exceeds a predetermined threshold; and
   means responsive to said detecting means for indicating poor contact between said patient electrode means and the patient.

3. The apparatus of claim 1 further including recording means coupled to the output of said fourth means for visually indicating the energy actually delivered to a patient.

4. The apparatus of claim 1 wherein said second means for sensing the magnitude of peak current includes:
   a transformer in the current path established by said patient electrode means; and
   a peak detector coupled to the output of said transformer.

5. The apparatus of claim 4 wherein said third means for determining actual transthoracic resistance includes:

first memory means, coupled to the output of said first means, for correlating values of stored energy to predetermined values of the reciprocal of the square root of stored energy;

means for multiplying the output from said first memory means and the peak current output from said peak detector; and second memory means coupled to the output of said multiplying means for correlating output values from said multiplying means to predetermined values of patient transthoracic resistance.

6. The apparatus of claim 5 further including:

means responsive to the output of said second memory means for detecting when values of transthoracic resistance exceed a predetermined threshold; and means responsive to said threshold detecting means for indicating poor contact between said patient electrode means and the patient.

7. The apparatus of claim 5 wherein said fourth means for determining energy actually delivered to a patient includes:

third memory means coupled to the output of said multiplying means for correlating output values to predetermined values representing the ratio of transthoracic resistance to total circuit resistance established in the current path from said high voltage storing means through said patient electrode means to the patient; and means for multiplying the output from said third memory means and the output of said first means for determining the magnitude of stored defibrillation energy.

8. The apparatus of claim 7 further including recording means responsive to said last-named multiplying means for visually indicating the portion of stored defibrillation energy actually delivered to a patient.

9. Apparatus for applying a preset quantity of stored defibrillation energy through a pair of electrodes to a patient comprising:

means for sensing the magnitude of peak current applied to a patient through said electrodes during a defibrillation shock pulse;

means responsive to said sensing means for normalizing said peak current magnitude to the square root of said preset quantity of stored defibrillation energy;

means responsive to said normalizing means for correlating the normalized peak current magnitude to a specific value of patient transthoracic resistance based on predetermined valuations;

means responsive to said correlating means for detecting when transthoracic resistance of a patient exceeds a predetermined threshold; and means responsive to said threshold detecting means for indicating poor contact between said electrodes and the patient.

10. The apparatus of claim 9 further including:

means responsive to said normalizing means for determining the proportion of said preset stored defibrillation energy actually delivered to the patient during defibrillation.

11. The apparatus of claim 10 wherein said sensing means includes:

a transformer in the current path established through said pair of electrodes; and a peak detector coupled to the output of said transformer.

12. The apparatus of claim 11 wherein said normalizing means includes:

memory means responsive to values of said preset quantity of stored defibrillation energy for relating said value of stored energy to predetermined values of the reciprocal of the square root of stored energy; and means for multiplying the output from said memory means and the peak current output from said peak detector.

13. The apparatus of claim 12 wherein said means for determining the proportion of preset stored defibrillation energy actually delivered to a patient includes:

memory means coupled to the output of said multiplying means for relating output values of normalized peak current to predetermined values representing the ratio of said transthoracic resistance to total circuit resistance established in the current path through said pair of electrodes to a patient; and means for multiplying the output from said last named memory means and the value of said preset stored defibrillation energy.

14. The apparatus of claim 13 further including recording means responsive to said last-named multiplying means for visually indicating the portion of stored defibrillation energy actually delivered to a patient.

* * * * *